Figure 1:
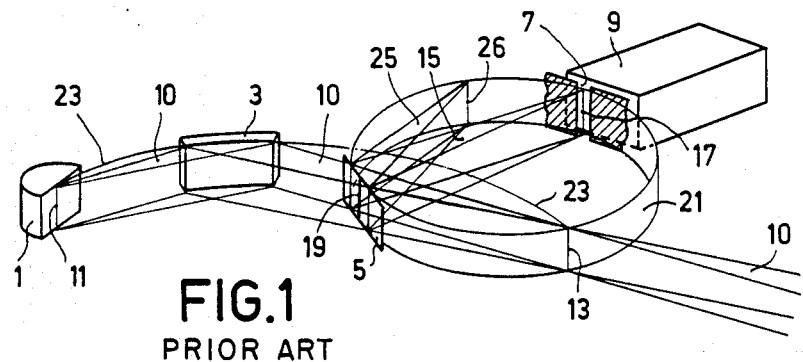

United States Patent [19]

Brouwer et al.

[11] Patent Number: 4,726,047
[45] Date of Patent: Feb. 16, 1988

[54] X-RAY ANALYSIS APPARATUS

[75] Inventors: Geert Brouwer; Sipke Wadman, both of Eindhoven, Netherlands

[73] Assignee: U.S. Philips Corporation, New York, N.Y.

[21] Appl. No.: 573,249

[22] Filed: Jan. 23, 1984

[30] Foreign Application Priority Data

Feb. 4, 1983 [NL] Netherlands ................. 8300420

[51] Int. Cl.⁴ .......................................... G01N 23/207
[52] U.S. Cl. ..................................... 378/73; 378/79; 378/81
[58] Field of Search ................... 378/73, 79, 81, 75, 378/72

[56] References Cited

U.S. PATENT DOCUMENTS 4,274,000  6/1981  Goebel .............................. 378/81

OTHER PUBLICATIONS

Dachs et al., "Guiner Camera for Single Crystal Investigation", Journal of Applied Crystalography (1972), vol. 5, pp. 338-342.

Primary Examiner—Carolyn E. Fields
Attorney, Agent, or Firm—Paul R. Miller

[57]    ABSTRACT

In an X-ray analysis apparatus, a specimen to be examined is mounted on the circumference of a focusing cylinder, which can be rolled along an auxiliary cylinder arranged concentrically around the beam focus of an X-ray beam. Independently of the movement mechanism used, a fixed part of the specimen then remains continuously in the beam path. Invariably the same surface area of the specimen is irradiated by the X-ray beam. The movement mechanism may have added to it a device by means of which during the movement of the specimen and the detector the detector is continuously optimally directed to the specimen. The specimen holder may have added to it a device for rotating and/or tilting a specimen included therein.

12 Claims, 9 Drawing Figures

U.S. Patent  Feb. 16, 1988  Sheet 1 of 3  4,726,047

X-RAY ANALYSIS APPARATUS

The invention relates to an X-ray analysis apparatus comprising an X-ray source, a monochromator, a displaceable preparation holder and a detector.

Such an X-ray analysis apparatus is known from Journal Appl. Crystallography 5, (1972), pp. 338–342. In a Guinier X-ray diffraction camera described therein, a preparation is moved during a measuring process along a straight line coinciding with the main ray of the X-ray beam. The detector consists of a film strip which is arranged along the focusing circle. In order to obtain a correct focusing of radiation diffracted by the preparation on the detector entrance, the preparation in such an apparatus must also invariably lie on the periphery of the focusing circle. The displacement of the preparation is to be carried out with great accuracy because the position and the orientation of the preparation in the beam directly influence the measuring accuracy. When the described method of moving the preparation along a ruler with a detector connected to a rotatably arranged arm is used, difficulties are met in given positions of the specimen.

The invention has for its object to provide an improvement in this respect; and for this purpose, according to the invention, an X-ray analysis apparatus of the kind mentioned in the opening paragraph is characterized in that the preparation upon displacement with respect to an analysing X-ray beam occupies a fixed position on a surface of a focusing cylinder that can be rolled about an auxiliary cylinder fixedly arranged around a beam focus of the analysing X-ray beam, while the detector can be rotated along the surface of the focusing cylinder.

Due to the fact that in an X-ray analysis apparatus according to the invention the preparation invariably forms part of a rolling cylinder, no unstable situations arise upon displacement thereof, but a continuous displacement is guaranteed. Due to the fact that the preparation occupies for each measuring position a fixed position on the circumference of a focusing circle coinciding with the focusing cylinder, a very correct angular positioning of the preparation with respect to the radiation beam is ensured. The method of displacement is moreover very suitable for an accurate independent angular measurement because due to the automatically correct angular orientation of the preparation and due to the positioning of the detector on the focusing cylinder, the angle between the incident beam and the detector can be directly measured. For measuring the angle between the detector and the radiation beam, in a preferred embodiment provision is made of an encoder.

In a preferred embodiment, an auxiliary cylinder forms part of a base plate and has a radius which is equal to the diameter of the focusing circle. The focusing cylinder is provided at an external surface with means by which it can be rolled in a slip-free manner along an internal surface of the auxiliary cylinder. Teeth co-operating in a slip-free manner are provided on the outer side of the focusing cylinder and on the inner side of the auxiliary cylinder.

In a further preferred embodiment, the focusing cylinder is provided with a concentrically arranged driving cylinder having, for example, a radius equal to half the radius of the auxiliary cylinder, and the focusing cylinder is displaced by means of, for example, a non-slipping belt transmission, for example, a toothed pulled and a rotary arm arranged so as to be rotatable about the axis of the auxiliary cylinder coinciding with the beam focus. The movement can again be realized entirely through toothed wheel transmission by the addition of another toothed wheel.

Use may also be made exclusively of standard toothed wheels. In a preferred embodiment, for this purpose the focusing cylinder is provided with a first driving cylinder arranged concentrically with respect to the focusing circle, and an additional cylinder having a circumference equal to that of the first driving cylinder is provided with a second driving cylinder arranged concentrically with respect to the additional cylinder and having a four times smaller circumference. The auxiliary cylinder fixedly arranged around the beam focus has a circumference whose value lies between those of the two driving cylinders.

A further embodiment comprises a first cylinder mounted around the beam focus, a second cylinder which is mounted concentrically with respect to the focusing circle and is located, for example, in part above the first cylinder, and two guide cylinders which engage the external surface of the first cylinder. By means of a belt transmission, from the first cylinder by the guide cylinders, the second cylinder, and hence the focusing circle, is rotated and rolled along the first cylinder in such a manner that the envisaged movement of the specimen is again obtained. A belt of the belt transmission co-operates in a slip-free manner with each of the cylinders, and is fixedly connected to each of them at such a point, and is arranged to surround each cylinder with such a pitch, that upon rotation no axial forces are produced. The belt, whose form and construction are further arbitrary, is wound around each of the cylinders with a number of turns which is inversely proportional to the diameter of the cylinders.

A few preferred embodiments according to the invention will now be described more fully with reference to the drawing.

Figure 2:
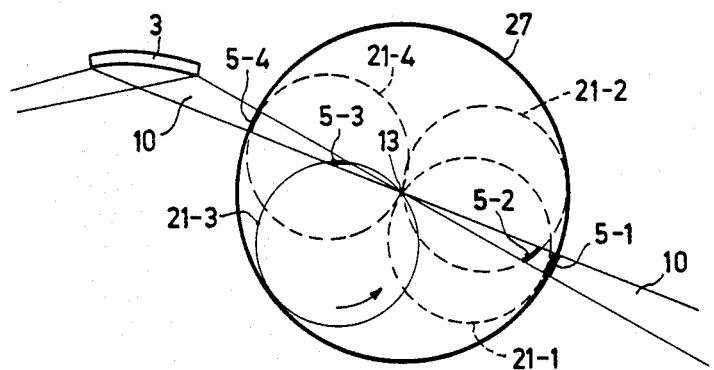
Figure 3A:
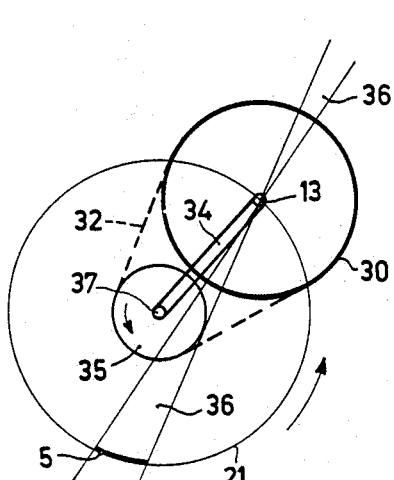
Figure 3B:
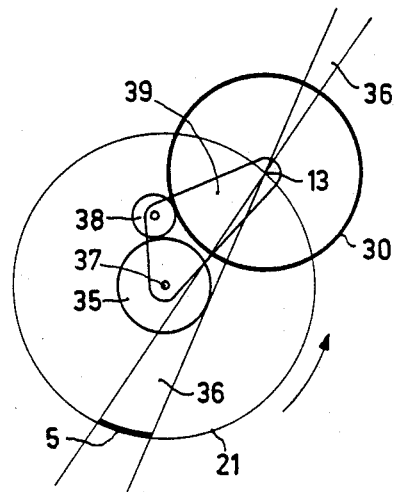
Figure 3C:
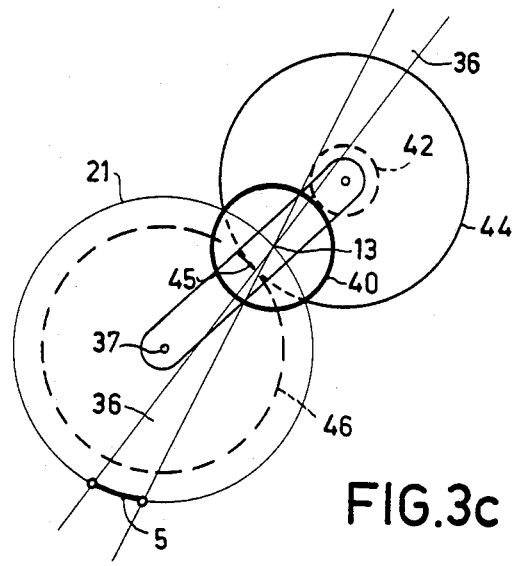
Figure 4A:
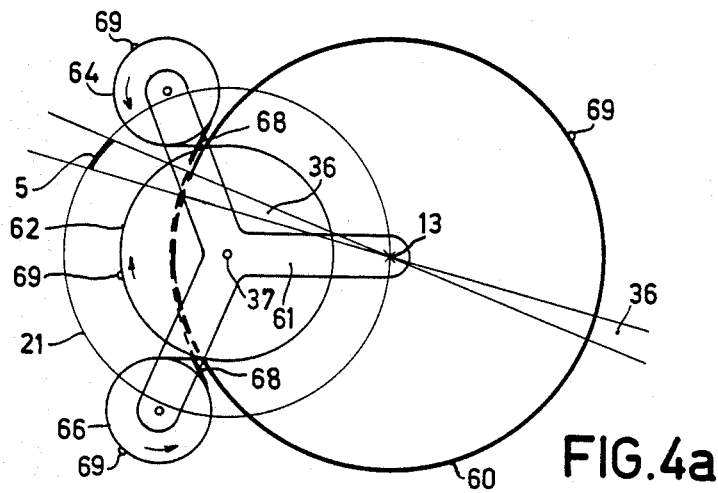
Figure 4B:
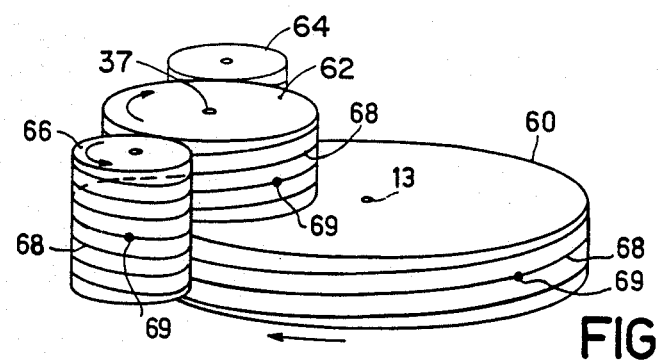
Figure 5A:
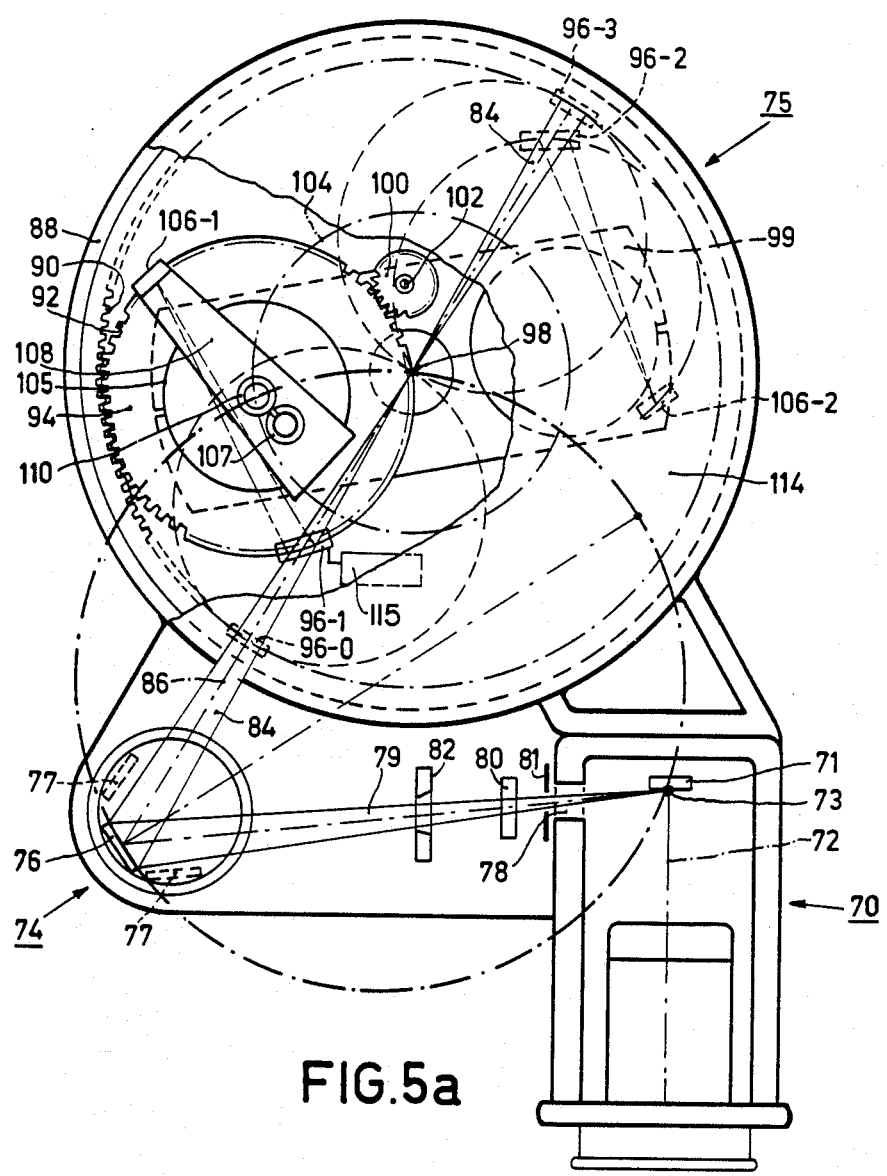
Figure 5B:
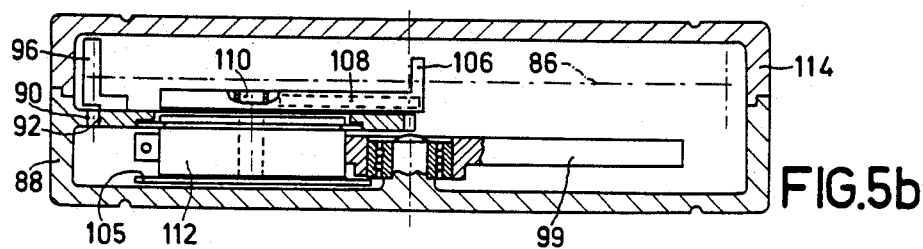

In the drawing:

FIG. 1 shows an outline of an X-ray analysis apparatus according to the prior art, FIG. 2 shows a basic outline of a displacement mechanism for an X-ray analysis apparatus according to the invention, FIGS. 3A, 3B, and 3C show basic outlines of further embodiments of such displacement mechanisms, FIGS. 4A and 4B show basic outlines of a displacement mechanism according to the invention with a belt transmission, and FIGS. 5A and 5B show a detailed outline of an X-ray analysis apparatus having a displacement mechanism of the kind shown in FIG. 2.

FIG. 1 shows for the sake of clarity the beam path in a type of X-ray analysis apparatus to which the invention relates. Of such an apparatus, an anode target 1 of an X-ray source, a monochromator crystal or a crystal holder 3, a preparation to be analysed or examined or a preparation holder 5, a detector entrance slit 7 and a detector 9 are shown. An X-ray beam 10 emanating from a line focus 11 on the anode target 1 is focused by the crystal in the crystal holder 3 in a focus line 13. A part 15 of the X-ray beam 10 diffracted in the preparation or specimen sample is focused in a focus line 17, and the detector slit 7 is arranged at the area of this line focus. The focus lines 13 and 17 and a line 19 of the specimen or preparation located centrally in the X-ray beam 10 all constitute surface lines of a focusing cylinder 21 assumed to be a physical cylinder in the case of a correct positioning. Similarly, the focus line 13 and the line focus 11 constitute surface lines of a focusing cylinder 23 of which the monochromator crystal in the crystal holder 3, which in this case is curved, for example, cylindrically, forms a segment. A beam 25 diffracted by crystal surfaces with mutually deviating crystal surface distances present in the preparation forms in a corresponding manner a focus line 26 on the focusing cylinder 21. When the detector 9 with the detector slits 7 is moved along the focusing cylinder 21, the preparation can be analysed for each position thereof or a diffractogram of a stationary preparation can be recorded. This may also be achieved in that the relevant part of the focusing cylinder is provided with a film strip. It is desirable for an extensive analysis of the preparation that the preparation can be displaced in the path of the beam 10. In order to obtain a correct beam focusing, the preparation then has to be continuously arranged so as to be tangent to, or so as to coincide with, the focusing cylinder.

FIG. 2 shows a preferred embodiment according to the invention the monochromator crystal in the crystal holder 3, the preparation holder 5 in four different positions, a cross-section of the X-ray beam 10 and the focusing cylinder 21, also in four positions. The preparation is displaced by means of an auxiliary cylinder 27 fixedly arranged around the beam focusing 13 and having a radius equal to the diameter of the focusing cylinder. The external surface of the focus cylinder is provided with means by which it can roll in a slip-free manner along an internal surface of the auxiliary cylinder 27 also provided with means for this purpose. When the focusing cylinder 21 rolls along the inner side of the auxiliary cylinder 27, the apparatus moves within the X-ray beam 10 between two extreme positions 5-1 and 5-4. During this movement, the part of the preparation irradiated with the X-ray beam 10 retains the same surface area due to the angular adaptation thus realized. It will be appreciated that, because the detector slit also coincides invariably with the focusing cylinder, the trajectory between the position 5-4 and the beam focus 13 is used for transmission measurements, while the trajectory between the beam focus 13 and the position 5-1 is used for reflection measurements. The focus 13, which consequently coincides with the axis of the auxiliary cylinder 27, remains a surface line of the focusing cylinder during the rolling movement. The continuous displacement of the preparation consequently comprises both the transmission trajectory and the reflection trajectory. During displacement, no unstable situations arise.

FIG. 3a shows a preferred embodiment of a displacement mechanism for a preparation. In this case it comprises an auxiliary cylinder 30 fixedly arranged around the beam focus 13. The auxiliary cylinder 30 is coupled via a slip-free belt transmission 32 to a cylinder 35 with a transmission of 1:2. The auxiliary cylinder 30 is further connected to the cylinder 35 via an arm 34 rotatable about the beam focus 13 and about an axis 37 of the cylinder 35. In order to obtain a displacement of an object 5 to be measured within a beam path 36 of an X-ray beam, the focusing cylinder 21 rotates together with the cylinder 35 with the focusing cylinder passing through the beam focus 13 and both cylinders rotating with the aid of the arm 34 about this point.

The embodiment shown in FIG. 3b is essentially equal to that of FIG. 3a with only the difference that instead of a belt transmission, an additional toothed wheel 38 between the now toothed cylinders 30 and 35 is utilized. The toothed wheel 38 has, for example, twenty teeth, while the cylinder 35 has, for example, forty-five teeth and the cylinder 30, which also in this case is fixedly arranged around the beam focus 13, has ninety teeth. The cylinders are coupled with each other via a connection member 39.

FIG. 3c shows an embodiment which can be entirely composed of standard toothed wheels. The embodiment shown comprises a toothed wheel 40 fixedly arranged around the beam focus 13 and having, for example, sixty teeth, which wheel is coupled via a toothed-wheel transmission to a toothed wheel 42 having thirty teeth. A toothed wheel 44 is mounted concentrically around the toothed wheel 42 and on the same shaft and this wheel is coupled via a toothed-wheel transmission 45 to a toothed wheel 46. The toothed wheels 44 and 46 have a transmission of 1:1 and in this embodiment each carry hundred and twenty teeth. The focusing cylinder 21, which is mounted concentrically around the last-mentioned toothed wheel 46 and on the shaft thereof and to which the preparation 5 is again fixedly secured, passes upon rotation of the toothed wheels through the beam focus 13, while a preparation 5 is then again displaced in the X-ray beam path 36 in a correct angular relationship. A yoke 45, to which the cylinders are rotatably connected, establishes a connection between the cylinders.

FIG. 4 shows an embodiment provided with a belt or cable transmission mechanism. In the sectional view of FIG. 4a, for this purpose a cylinder 60 fixedly arranged around the beam focus 13 and having, for example, a diameter of 200 mm, a cylinder 62 moving along it and having a diameter of 100 mm and two auxiliary cylinders 64 and 66 each having a diameter of 50 mm thereof are shown. A belt 68, which is fixedly connected to each of the cylinders in a point 69, couples the cylinders to each other in a slip-free manner indicated in FIG. 4b. Due to the fact that the cylinders are provided with helical guides for the belt, whose pitch per cylinder is inversely proportional to the diameter thereof with, the sign of the pitch of the cylinders 64 and 66 being opposite to that of the cylinders 60 and 62, the same displacement of the belt in the direction of height occurs upon rotation at each cylinder so that no axially directed forces will be produced. The assembly of the cylinder 62 and the auxiliary cylinders 64 and 66 is rotated during the movement of the belt about the fixed cylinder 60, the focusing cylinder 21 mounted around the cylinder 62 again passing through the beam focus 13 of the X-ray beam and the object to be examined again performing a linear displacement within the radiation path 36 of the X-ray beam. A yoke 61 in this case ensures connection between the cylinders.

The extent of the rotation, expressed, for example, in the angular movement around the beam focus, can be chosen by adaption of the movement of the belt. If only a rotation of well over 90° is desired, a short and comparatively simple belt movement mechanism is sufficient. With a sufficiently long belt, however, a rotation up to well over 360° can also be realized.

In order to ensure that the detector is continuously directed to the specimen, a detector rotation device can be added to each of the movement mechanisms to be used. This device ensures that the direction of the detector turns back with respect to the focusing circle upon rotation about a given angle over half that angle, as a result of which the detector upon rotation about the center of the focusing circle is nevertheless constantly directed to the specimen located on the circumference thereof. This may be realized, for example, by means of a belt transmission driven by the driving cylinder or via an additional toothed wheel.

In a preferred embodiment, the preparation holder has added to it a movement mechanism 115 shown in FIG. 5A which permits rotating a preparation provided in the holder in the plane thereof through a known angle. This rotation may be of special importance with texture examination, because then, the maximum intensity directly connected therewith and hence the direction of the maximum texture can be determined. For this purpose, the preparation holder need only be provided with a shaft to be driven. For the drive use may be made of a motor 115 following the movement of the preparation holder 5 or of a drive via a motor that can be decoupled elsewhere. Alternatively, the preparation holder may have added to it a movement mechanism for realizing a tilting movement of a preparation, whereby the shaft directed at right angles to the preparation is moved out of the plane of the focusing circle.

FIG. 5 shows a mechanically detailed outline of an apparatus according to the invention, for example, an apparatus for X-ray powder diffraction, for stress examination, texture examination or for another examination directly correlated to the crystal structure.

An outline of such an apparatus partly broken away, indicated in FIG. 5a, shows an X-ray tube 70 having an anode target 71 on which an electron beam 72 produces a linear target surface 73 at right angles to the plane of the drawing, a monochromator housing 74 and a goniometer housing 75. The monochromator housing comprises a monochromator crystal 76, which is arranged so that it may be rotated away in order that it may be replaced by a crystal 77 for radiation of a different wavelength, for which purpose the X-ray tube is exchangeable or is provided with two different target materials. The two crystals 76 and 77 may be free of dislocations. For example, the anode of the tube may comprise a target of copper for producing copper K $\alpha$ 1 radiation having a wavelength of 0.154 nm and a target of chromium for producing chromium K $\alpha$ 1 radiation having a wavelength of 0.299 nm, which are to be individually irradiated.

In a beam path of an X-ray beam 79 emanating from an X-ray tube 70 there can be arranged an attenuation filter 80, a shutter 81 and a beam diaphragm 82. The diaphragm 82 is, for example, in the form of a slit having a longitudinal direction at right angles to the plane of the drawing, but it may also be constructed so that a part is screened in another direction. In order to limit as far as possible reflections at the diaphragm edges also with a thicker diaphragm, it may be favourable to form the diaphragm from, for example, a planar silicon single crystal cut along (111) crystal surfaces. The X-ray beam 79 strikes the monochromator crystal 76, which is, for example, a curved Si single crystal. In a preferred embodiment, the apparatus comprises a silicon single crystal in a form as described in the co-pending Patent Application Ser. No. 573,244, filed Jan. 23, 1984, and assigned to the same assignee as the present application. An X-ray beam 84 chromatized by crystal surfaces of the crystal enters through a window 86 the goniometer housing. The goniometer part, which is shown in cross-section in FIG. 5b, comprises a cylinder 88 which in this case is provided on the inner-surface. These teeth cooperate in a slip-free manner with teeth 92 which are provided at an outer periphery of a focusing cylinder 92. For displacement of a specimen 96 to be examined, which is again fixedly secured to the focusing cylinder 44, the cylinder 94 is rolled along the pitch circle of the inner teeth of the fixed cylinder 88 between two extreme positions 96-0 and 96-3 for the specimen. The specimen is then moved in the beam path of the X-ray beam 84 for transmission examination from the first extreme position 96-0 opposite the entrance window 86 against the cylinder 88 via an intermediate position 96-1 to a beam focus 98 of the beam and is continuously moved for reflection examination from the beam focus 98 via an intermediate position 96-2 to the position 96-3 diametrically opposite the entrance window. For driving the rolling movement, use is made here of an additional toothed wheel 100 which is driven by a motor drive (not shown) mounted on a mounting board 99 and which co-operates also with the teeth 92 of the focusing cylinder 94. A shaft 102 of the toothed wheel 100 is then displaced with respect to the fixed cylinder 88 again along a circle. A shaft 110 of the focusing cylinder 94 moves along a circle 104 around the beam focus 98. A detector 106 is mounted on the circle circumference of the focusing circle 94 and is rotatably coupled via an arm 108 to the shaft 110 of the focusing cylinder 94. For each position of the focusing cylinder 94, the detector 106 can be moved along the circumference thereof, as a result of which use may be made, for example, of a driving motor (not shown) also mounted on the mounting board 99. By means of this motor, a detector supporting disk 105 is driven via the shaft 110. This movement can be performed in each position of the specimen. By means of an encoder 112, for example, the angle between the incident beam and the detector can invariably be measured with great accuracy. In fact, the encoder therefore measures an angle 4 $\theta$, where $\theta$ represents the Bragg angle for a preparation in a measuring position. Also in this case, the addition of a further toothed wheel or another suitable coupling or driving mechanism 107 can ensure that the detector 106 is continuously readjusted upon rotation of the preparation and the detector so that the detector is continuously orientated so as to be directed to the preparation. By means of a cover part 114, the entire movement mechanism can be closed, as a result of which the space within this mechanism may be conditioned with the housing for the monochromator crystal. Due to the high degree of freedom in the choice of the position of the specimen, the latter can now also be positioned so that a dispersion occurring in the X-ray beam at the monochromator crystal or already before it can be at least partly compensated or amplified by dispersion at the specimen.

What is claimed is:

1. An X-ray analysis apparatus comprising
an X-ray source providing an X-ray beam,
monochromator means for focusing said X-ray beam in a line focus,
displaceable preparation holder means for holding a specimen,
a focusing cylinder movable in said X-ray beam to place said specimen in fixed positions in said X-ray beam,
an auxiliary cylinder fixedly arranged around a beam focus of said X-ray beam, said focusing cylinder being rollable about said auxiliary cylinder so that said specimen retains the same surface area irradiated by said X-ray beam, wherein said auxiliary cylinder has a radius equal to the diameter of said focusing cylinder, and wherein said focusing cylinder is rollable in a slip-free manner along an internal surface of said auxiliary cylinder, and detector means rotatable along a surface of said focusing cylinder for detecting said X-ray beam.

2. An X-ray apparatus according to claim 1, wherein encoder means are provided for making angular measurements between said X-ray beam and said detector means for each position of said specimen.

3. An X-ray analysis apparatus according to claim 1, wherein said internal surface of said auxiliary cylinder and the external surface of said focusing cylinder are provided with teeth co-operating in said slip-free manner.

4. An X-ray analysis apparatus according to claim 1 or claim 2, wherein said focusing cylinder is provided with a concentrically arranged driving cylinder coupled by a slip-free belt to said auxiliary cylinder, said auxiliary cylinder being fixedly arranged around said beam focus, and said auxiliary cylinder having a radius equal to the diameter of said driving cylinder.

5. An X-ray analysis apparatus according to claim 1 or claim 2, wherein said focusing cylinder is provided with a concentrically arranged driving cylinder having an external surface with teeth, said driving cylinder being coupled to said auxiliary cylinder by an intermediate toothed wheel, said auxiliary cylinder being externally provided with a number of teeth being twice that of said driving cylinder, and said auxiliary cylinder being fixedly arranged around said beam focus.

6. An X-ray apparatus according to claim 1 or claim 2, wherein said auxiliary cylinder co-operates with an intermediate wheel under a transmission ratio of 1:2, said intermediate wheel being concentrically connected to a first cylinder, said first cylinder cooperating with a second cylinder arranged concentrically with said focusing cylinder, said first and second cylinders having equal diameters.

7. An X-ray analysis apparatus according to claim 1 or claim 2, wherein said auxiliary cylinder is coupled by a belt transmission, by a first intermediate cylinder, and by two smaller diameter cylinders to said focusing cylinder, said belt transmission having at least a point in contact with said auxiliary cylinder, said first intermediate cylinder, and said two smaller diameter cylinders, said first intermediate cylinder being concentrically mounted with said focusing cylinder, and said belt transmission passing through a guide to eliminate axial force upon rotation.

8. An X-ray analysis apparatus according to claim 1 or claim 2, wherein said preparation holder means and said detector means are moved by means for continuously directing said detection means to said specimen during a measurement sequence.

9. An X-ray analysis apparatus according to claim 1 or claim 2, wherein said monochromator means includes a double focusing monochromator crystal, said crystal being a single crystal substantially free of dislocations.

10. An X-ray analysis apparatus according to claim 1 or 2, wherein said preparation holder means is moved by means for rotating said specimen about an axis at right angles to a surface of a crystal to be irradiated, said axis lying in a plane of a focusing circle.

11. An X-ray analysis apparatus accordng to claim 1 or claim 2, wherein said preparation holder means includes means for tilting said specimen with respect to an axis at right angles to a surface of a crystal to be irradiated, said axis lying in a plane of a focusing circle.

12. An X-ray analysis apparatus according to claim 1 or claim 2, wherein a beam stopping diaphragm for said X-ray beam includes a slice of a single crystal substantially free of dislocations, said single crystal being cut along (111) crystal surfaces.

* * * * *